(12) United States Patent
Styrc

(10) Patent No.: US 7,785,364 B2
(45) Date of Patent: Aug. 31, 2010

(54) KIT TO BE IMPLANTED IN A BLOOD CIRCULATION CONDUIT

(75) Inventor: Mykolaj Styrc, Kopstal (LU)

(73) Assignee: Laboratoires Perouse, Ivry le Temple (FR)

( * ) Notice: Subject to any disclaimer, the term of this patent is extended or adjusted under 35 U.S.C. 154(b) by 36 days.

(21) Appl. No.: 12/155,617

(22) Filed: Jun. 6, 2008

(65) Prior Publication Data

US 2008/0319538 A1    Dec. 25, 2008

(30) Foreign Application Priority Data

Jun. 8, 2007    (FR) .................................... 07 55603

(51) Int. Cl.
*A61F 2/06* (2006.01)
(52) U.S. Cl. ...................... 623/1.24; 623/1.15
(58) Field of Classification Search ............... 623/1.15, 623/1.24, 2.11, 1.25, 1.26, 23.7, 2.1–2.29, 623/2.35–2.42; 138/45, 46, 108
See application file for complete search history.

(56) References Cited

U.S. PATENT DOCUMENTS

| | | | |
|---|---|---|---|
| 5,411,552 A * | 5/1995 | Andersen et al. ........... 623/2.18 |
| 6,425,916 B1 | 7/2002 | Garrison et al. | |
| 2002/0032481 A1 | 3/2002 | Gabbay | |
| 2002/0151970 A1 | 10/2002 | Garrison et al. | |
| 2003/0149477 A1 | 8/2003 | Gabbay | |
| 2005/0004665 A1 | 1/2005 | Aklog | |
| 2005/0004668 A1 | 1/2005 | Aklog et al. | |
| 2005/0080483 A1 * | 4/2005 | Solem et al. ............... 623/2.11 |
| 2007/0198097 A1 | 8/2007 | Zegdi | |

FOREIGN PATENT DOCUMENTS

| | | |
|---|---|---|
| EP | 0 850 607 | 7/1998 |
| FR | 2 883 721 | 4/2005 |
| WO | 00/47139 | 8/2000 |
| WO | 2005/070343 | 8/2005 |
| WO | 2007/009609 | 1/2007 |

* cited by examiner

*Primary Examiner*—Corrine M McDermott
*Assistant Examiner*—Matthew Schall
(74) *Attorney, Agent, or Firm*—Wenderoth, Lind & Ponack, L.L.P.

(57) ABSTRACT

A kit includes a tubular endoprosthesis having an inner surface which delimits a channel with a longitudinal axis. The kit includes a prosthetic valve to be implanted in the channel. The valve includes a supporting framework having an outer surface to be applied against the inner surface, and a flexible obturator which is connected to the framework. The endoprosthesis includes a stop for locking the supporting framework in order to block the axial displacement of the outer surface along the inner surface in at least a first direction. The stop includes at least one flexible connection extending transversely in the channel between two connection points, which are located on the inner surface and are angularly spaced about the axis.

13 Claims, 4 Drawing Sheets

KIT TO BE IMPLANTED IN A BLOOD CIRCULATION CONDUIT

TECHNICAL FIELD

The present invention relates to a kit to be implanted in a blood circulation conduit. The kit is of the type comprising a tubular endoprosthesis having an inner surface which delimits a channel with a longitudinal axis; and a prosthetic valve which can be moved relative to the tubular endoprosthesis in order to be implanted in the channel. The prosthetic valve includes a supporting framework having an outer surface to be applied against the inner surface of the endoprosthesis, the framework being radially deformable from a folded fitting position to a deployed implantation position. The valve also includes a flexible obturator which is connected to the framework, and which is deformable between a closure position in which it extends transversely, and a release position in which it is contracted transversely due to the flow circulating in the channel. The endoprosthesis comprising at least one stop for locking the prosthetic valve in the channel in order to block axial displacement of the outer surface along the inner surface in at least a first direction.

A kit comprising a tubular endoprosthesis and prosthetic valve which has a deformable supporting framework and a flexible obturator fixed on the framework is known from EP-A-850 607.

A kit of this type is intended to be implanted to replace a valve in a blood circulation conduit.

Valves of this type are located, for example, in the heart between the atria and the ventricles, or at the outlet of the right ventricle and of the left ventricle. These valves ensure the blood flow circulates in one direction, preventing a reflux of blood following a ventricular contraction.

In order to replace a valve, the tubular endoprosthesis provided in the kit is implanted in the portion of the conduit in which the diseased valve is located. The prosthetic valve is subsequently conveyed, in its folded state, in the inner channel delimited by the endoprosthesis and is applied against the endoprosthesis by inflating a balloon.

A device of this type is not entirely satisfactory. More specifically, the prosthetic valve can only be positioned relative to the endoprosthesis in an approximate manner, and the valve is not securely fixed in the endoprosthesis.

In order to overcome this drawback, FR-A-2 883 721 discloses a kit of the aforementioned type in which the stops for locking the prosthetic valve are formed by deforming the supporting framework in order to produce portions having variable cross-sections along the longitudinal axis. The outer surface of the supporting framework is thus wedged between a distal stop and a proximal stop when the valve is implanted in the endoprosthesis.

A kit of this type is not entirely satisfactory. More specifically, the tubular framework of the endoprosthesis comprising the stops may be difficult to produce. In addition, the transverse stops formed in the framework increase the radial size of the endoprosthesis when it is inserted into the body of the patient, since the stops limit the extent to which the endoprosthesis can be compressed radially in the insertion tool thereof.

SUMMARY OF THE INVENTION

An object of the invention is thus to provide a kit of the aforementioned type which allows a prosthetic valve to be implanted precisely and securely in a tubular framework previously implanted without increasing the radial size of the framework when it is inserted into the body of the patient.

For this purpose, the invention relates to a kit of the aforementioned type, wherein the stop comprises at least one flexible connection extending transversely across the channel between two connection points which are located on the inner surface and are spaced angularly about the longitudinal axis.

The kit according to the invention may comprise one or more of the following characteristics, taken in isolation or in accordance with any technically achievable combination. The tubular endoprosthesis can be deployed between a compressed state and a dilated state, with each flexible connection being deployable in conjunction with the endoprosthesis between a slack configuration when the endoprosthesis is in the compressed state and a tight position across the channel when the endoprosthesis is in its dilated state. Each flexible connection can be free relative to the inner surface between its connection points. The connection points of each flexible connection can extend substantially in the same plane perpendicular to the longitudinal axis. Each stop can comprise at least two flexible connections, each extending between two connection points, the connection points forming the vertices of a polygon. The endoprosthesis can comprise a proximal stop and a distal stop which are at a distance from one another in the axial direction, each stop comprising at least a flexible connection extending transversely across the channel between two connection points which are located on the inner surface and are spaced angularly about the longitudinal axis. Each connection of at least one stop can delimit a central passage in the channel, the supporting framework of the prosthetic valve, in its folded fitting position, being able to be inserted between the distal stop and the proximal stop through the central passage. The axial distance separating the proximal stop and the distal stop can be greater than or substantially equal to the length of the outer surface placed in contact with the inner surface, taken along the longitudinal axis, and each flexible connection can be formed by a thread.

BRIEF DESCRIPTION OF THE DRAWINGS

A clearer understanding of the invention will be facilitated by the description below given solely by way of example and with reference to the appended drawings, in which.

DESCRIPTION OF PREFERRED EMBODIMENTS

Figure 1:
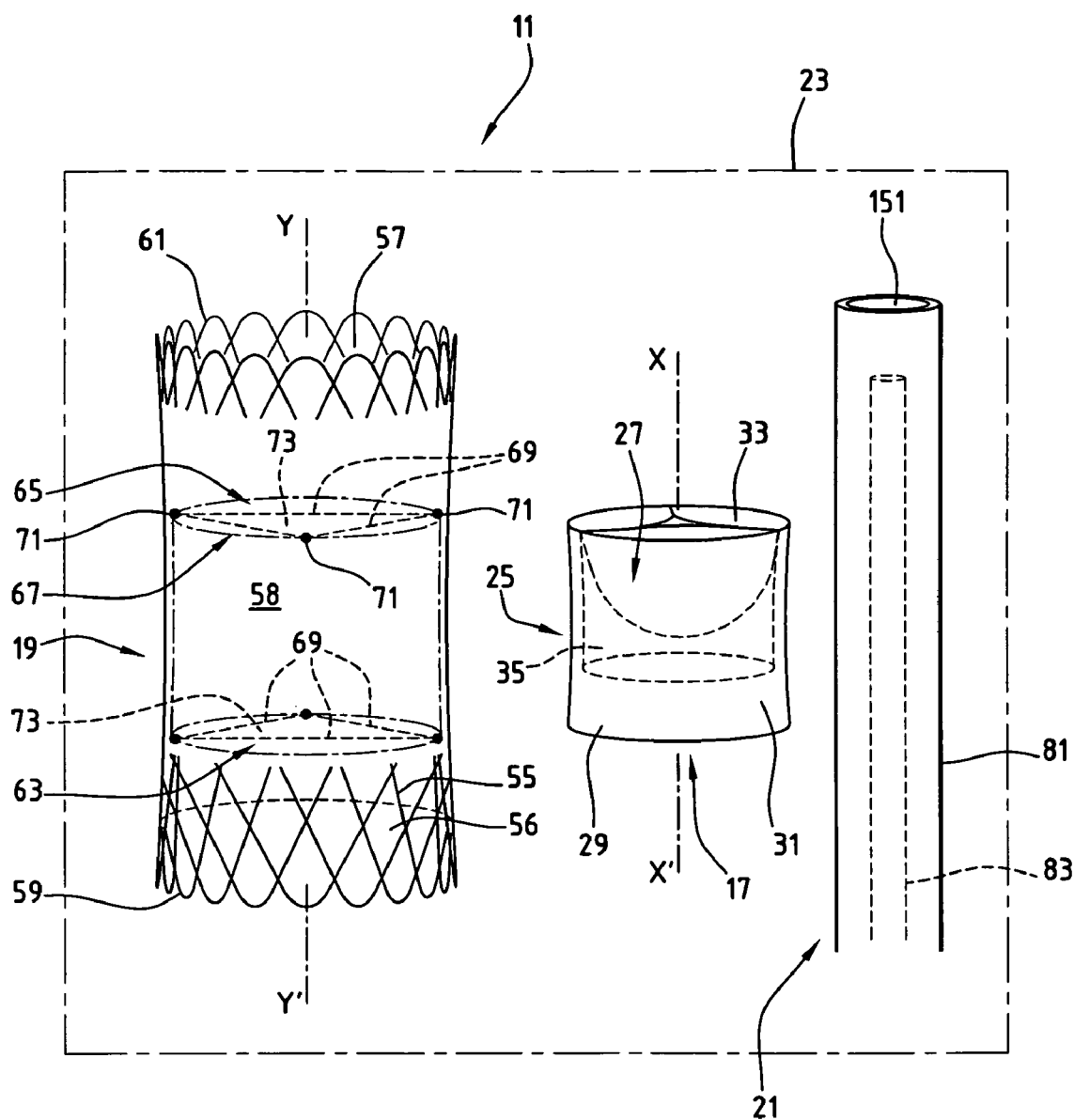
FIG. 1 is a partial schematic perspective view of a first kit according to the invention prior to being implanted in a blood vessel.
Figure 2:
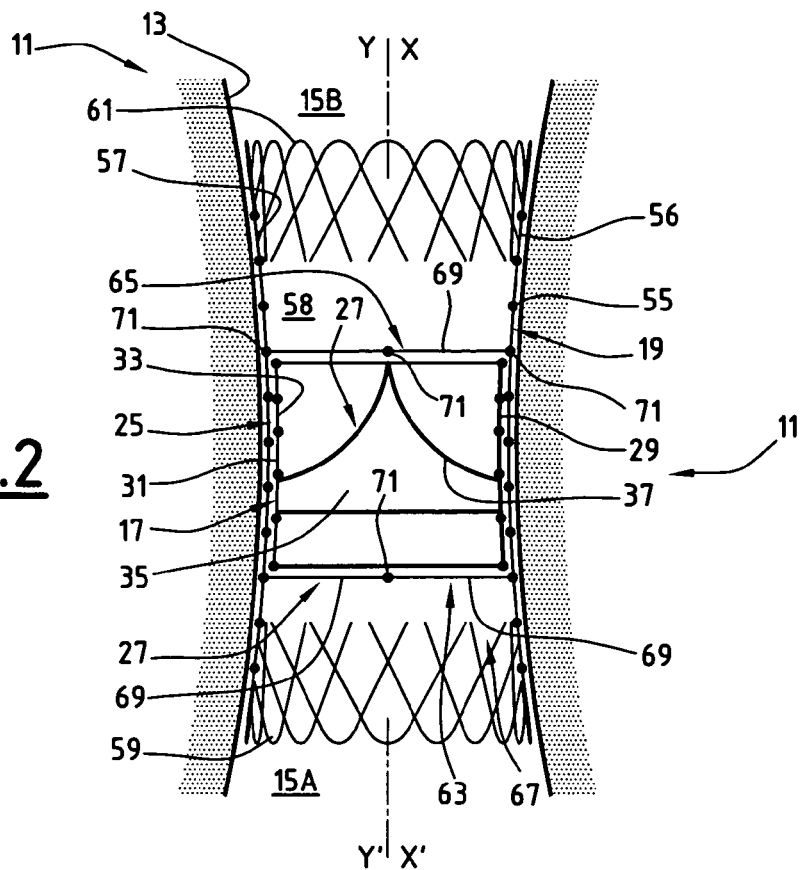
FIG. 2 is a cross-section along an axial median plane of the first kit according to the invention implanted in a blood circulation conduit.
Figure 3:
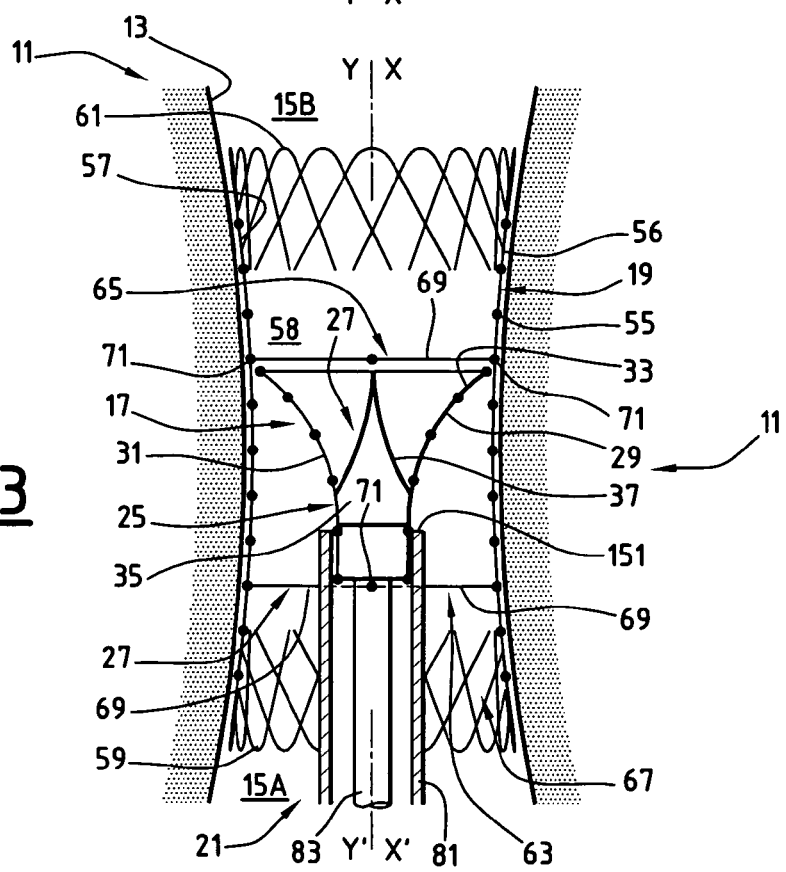
FIG. 3 is a view analogous to that of FIG. 2 during implantation of the prosthetic valve in the endoprosthesis.

A first kit 11 according to the invention is shown in FIGS. 1 to 3.

FIG. 1 shows the kit 11 prior to being implanted in a blood circulation conduit, whereas FIG. 2 shows the kit 11 implanted in a blood circulation conduit 13. The conduit 13 is, for example, a pulmonary artery connected at its proximal end 15A to the outlet of the right ventricle of the heart, in particular in a human being, and connected at its distal end 15B to the lung.

As shown in FIG. 1, the kit 11 comprises a prosthetic valve 17, an endoprosthesis 19 intended to receive the prosthetic valve 17 and a tool 21 for implanting the prosthetic valve 17 in the endoprosthesis 19.

The kit 11 is stored in packaging 23 for example.

As shown in FIG. 2, the prosthetic valve 17 comprises a supporting framework 25 and a deformable obturator 27 which is supported by the framework 25 and is integral therewith.

When the valve 17 is fitted in the endoprosthesis 19, this valve 17 can move relative to the endoprosthesis 19 between an initial storage position at a distance from the endoprosthesis 19, shown in FIG. 1, and a position fitted in the endoprosthesis 19, shown in FIG. 2.

The framework 25 is formed by a self-expanding tubular lattice which has an axis X-X' and can be deployed spontaneously between a folded fitting configuration having a small radial diameter and a deployed configuration having a large radial diameter. The tubular lattice 29 delimits an outer peripheral surface 31, which is applied against the endoprosthesis 19 when the valve 17 is fitted therein, and an inner peripheral surface 33 on which the obturator 27 is fixed. The obturator 27 is formed, for example, from a valve belonging to a bovine or ovine animal. In a variant, it is formed from natural or synthetic tissue.

The obturator 27 comprises a tubular base 35 which is fixed on the inner surface 33 and is extended upwards by three closure laminae 37.

The laminae 37 are formed in one piece with the base 35 and are distributed about the axis X-X'. The laminae 37 can be deformed between a closure configuration, in which they substantially close off the inner lumen 44, and a release configuration in which they are positioned against the tubular lattice 29 in order to allow blood to pass through the valve 17.

The endoprosthesis 19 is formed from a tubular lattice having a central axis Y-Y' made of interlaced threads 55 which are embedded in an extendable film 56 which is liquid-tight, such as an elastomer.

The lattice 55 is obtained by weaving at least one stainless steel thread, a shape-memory alloy thread or a polymer thread. In a variant, the lattice 55 is obtained by laser cutting a tube.

As is known per se, the lattice 55 of the endoprosthesis is capable of spontaneously deforming from a compressed state, in which it has a small diameter, to a dilated state, in which it has a greater diameter, said dilated state constituting the rest state thereof.

In the implanted state as shown in FIG. 2, the endoprosthesis 19 is applied, due to the resilience thereof, against the inner surface of the conduit 13, thus forming a sheath inside the conduit 13.

The endoprosthesis 19 has an inner surface 57 which delimits a channel 58 for circulation of the blood flow, and having an axis Y-Y' and opening out at the proximal end 59 and the distal end 61 of the endoprosthesis 19.

The inner surface 57 of the endoprosthesis is generally continuously derivable in such a way that the channel 58 delimits a continuous variable cross-section from the proximal end 59 towards the distal end 61 of the endoprosthesis 39.

The endoprosthesis 19 comprises a proximal stop 63 and a distal stop 65 for locking the valve 17 in order to prevent the valve 17 from being displaced axially towards the proximal end 59 and towards the distal end 61 respectively of the tubular lattice 55. As shown in FIGS. 1 to 3, each stop 63, 65 is formed by a transverse construction 67 of filamentary connections in the form of a polygon which can be deployed in the circulation channel 58 of the blood flow. The proximal stop 63 is offset axially relative to the distal stop 65. The distance separating the stops 63, 65 along the axis Y-Y' is greater or substantially equal to the length of the outer surface 31 of the tubular lattice 29, as shown in FIG. 2.

In the example shown in FIG. 1, each stop 63, 65 is formed by three filamentary connections 69 in the form of a triangle which are flexible so that they can be deployed between a slack configuration when the endoprosthesis 19 is inserted into the human body and a tight configuration after the endoprosthesis 19 has been deployed in its dilated state.

In this example, each filamentary connection 69 is composed of a thread which is fixed at the ends thereof onto the inner surface 57 of the endoprosthesis 19 at two connection points 71 by means of fasteners. Between its ends, each filamentary connection 69 is also free relative to the inner surface 57. The points 71 for connecting the filamentary connections 69 are distributed angularly about the axis Y-Y' of the endoprosthesis 19 and are located substantially in the same transverse plane relative to the axis Y-Y'.

The construction of the filamentary connections 69 extends in a transverse plane when the filamentary connections 69 are deployed in the channel 58. The connection points 71 thus form the vertices of a polygon, the sides of which are delimited by the connections 67.

In the channel 58, the filamentary connections 69 delimit a central circulation passage 73 which is open for the tool 21 for implanting the valve 17 in the conduit 58 to be inserted, as described below.

The filamentary connections 69 are formed, for example, from stainless steel, a polymer or a shape-memory metal. They have a small diameter, at least ten times smaller than the diameter of the channel 58 when the endoprosthesis 19 is in its dilated state.

The implantation tool 21 comprises a catheter 81 for holding the valve 17 in the retracted configuration thereof and a stent 83 for pushing the valve 17 to be inserted in the catheter 81. The catheter 81 has an inner cross-section which is smaller than the cross-section of the valve 17 in its deployed configuration, and an outer cross-section which is smaller than the inner cross-section of the endoprosthesis 19 and smaller than the inner cross-section of the central passage 73 which is delimited between the filamentary connections 69 of the proximal stop 63 and the distal stop 65. The stent 83 can be displaced axially within the catheter 81. Its distal end supports the valve 17 before it is implanted in the endoprosthesis 19.

The mode of operation of the first kit 10 according to the invention will now be described. The surgeon initially loads the valve 17 into the implantation tool 21. For this purpose, he fixes the valve 17 relative to the stent 83 and radially retracts the valve 17 to cause it to pass into the catheter 81, as is known per se. The supporting framework 25 of the valve 17 is thus compressed between the stent 83 and the catheter 81 in its small-diameter configuration in preparation for it to be inserted into the human body.

The surgeon similarly contracts the endoprosthesis 19 so it is in the compressed state in an insertion tool (not shown). When the endoprosthesis 19 is in the compressed state, the flexible filamentary connections 69 of the stops 63, 65 are slack in the central channel 58. The filamentary connections 69 take up very little volume in the channel and since the inner surface of the lattice 55 does not have discontinuities of a large size, it is possible to contract the endoprosthesis 19 radially in order to greatly decrease its size when inserted into the patient.

The surgeon thus inserts the endoprosthesis 19 into the body of the patient in a known manner by the percutaneous route until it reaches its implantation position in the conduit 13. He then unfurls the endoprosthesis 19 in the conduit by expanding it radially towards the dilated state thereof. The lattice 55 of the endoprosthesis thus flattens out against the wall of the conduit 13.

When the endoprosthesis is deployed, the filamentary connections 69 of the stops 63, 65 become tight. The transverse constructions 67 of filamentary connections in the form of a polygon are thus deployed across the channel 68 to form the stops 63, 65. Each connection 69 thus extends in a linear manner, substantially in a plane perpendicular to the axis Y-Y' in the channel 58 at a distance from the inner surface 57, with the exception of at the connection point 71.

As shown in FIG. 3, the tool 21 is thus inserted into the body of the patient by the percutaneous route while holding the valve 17 in a contracted state between the stent 83 and the catheter 81. The tool 21 is thus positioned in such a way that its distal end is inserted into the inner channel 58 of the endoprosthesis 19 between the stops 63, 65 and through the central passage 73 delimited by the filamentary connections 69 of the proximal stop 63.

This having been achieved, the catheter 81 is displaced in a proximal manner relative to the stent 83 which is held in position between the stops 63, 65. The displacement of the catheter 81 progressively exposes the supporting framework 25 of the valve 17 and causes the distal edge of said framework to expand radially into the channel 58. The distal edge of the framework 25 thus has an outer diameter which is greater than the maximum cross section of the passage 73 which is delimited between the filamentary connections 69 of the distal stop 65. The surgeon thus displaces the valve 17 by the stent 83 until the distal edge of the framework 25 abuts the filamentary connections 69 of the distal stop 65.

The surgeon then completely exposes the framework 25 and thus releases the proximal edge of the valve 17. The outer surface 31 of the framework is wedged against the inner surface 57 of the endoprosthesis 19. In addition, the framework 25 is wedged axially between the proximal stop 63, which prevents it from being displaced in a first direction towards the proximal end 59 of the endoprosthesis 19, and the distal stop 65, which prevents it from being displaced in a second direction towards the distal end 61 of the endoprosthesis 19.

The valve 17 is thus very precisely positioned in the endoprosthesis 19. It is held in position axially in a secure and durable manner by the stops 63, 65 formed by the filamentary connections. The axis X-X' of the lattice 23 is substantially coaxial with the axis Y-Y' of the lattice 55.

In addition, the small area occupied by the stops 63, 65 prevents the blood flow through the kit 11 from being substantially reduced. Furthermore, the stops 63, 65 are produced in a simple and inexpensive manner without having to modify the construction of the lattice of the endoprosthesis 19.

The implanted prosthetic valve 17 functions as described below. At the end of an expulsion procedure by the right ventricle, when said ventricle increases in volume, the blood flow is drawn up into the conduit 13 from the distal end 15B towards the proximal end 15A. The blood thus fills the laminae 37 which are displaced radially towards the axis X-X', thus closing the conduit 13 in a substantially liquid-tight manner.

When the right ventricle contracts, the blood circulates from the proximal end 15A towards the distal end 15B. The laminae 37 are thus flattened against the inner surface 33 of the supporting framework 25, which causes the channel 58 to open. The blood flow is thus free to circulate in the conduit 13 on either side of the valve 17.

Figure 4:
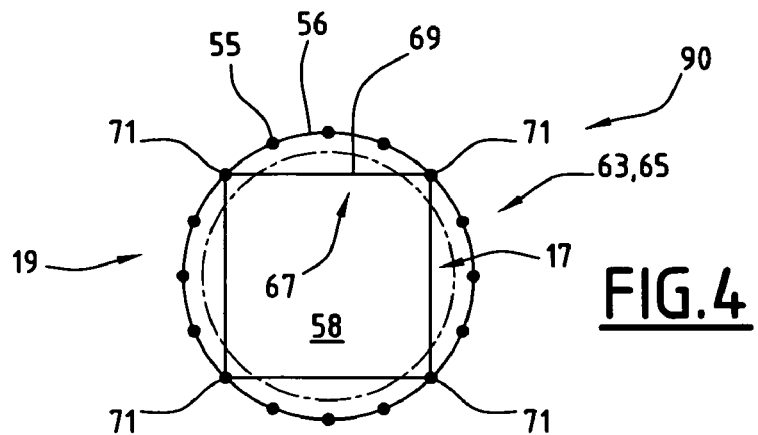
FIG. 4 is a sectional view along a transverse plane of a second kit according to the invention.

In the second kit 90 according to the invention, shown in FIG. 4, each stop 63, 64 is formed by a polygon comprising at least four sides.

In another variant, the polygonal construction 67 is formed by a single closed thread engaged across the lattice at the connection points 71. The single thread delimits a closed polygon and occupies a generally invariant position relative to the endoprosthesis 19.

Figure 5:
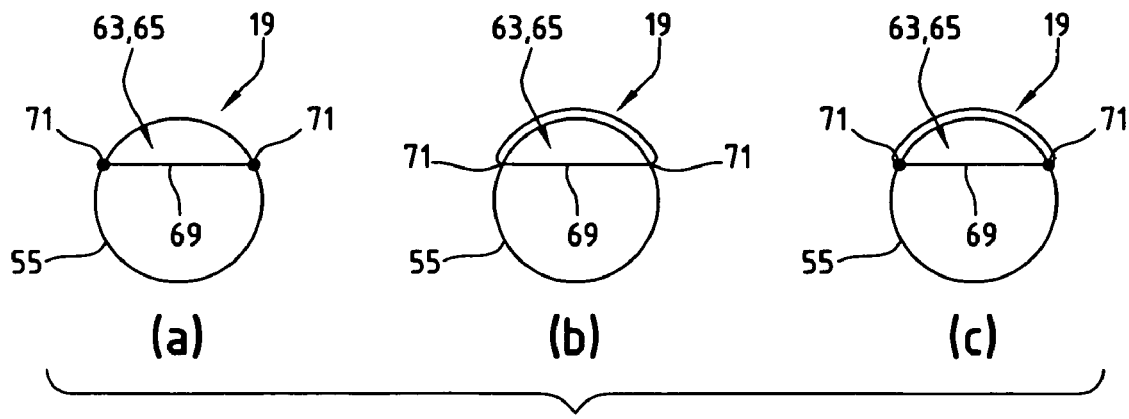
FIGS. 5 to 7 are views analogous to that of FIG. 4 of variants of the second kit.

FIG. 5 shows variants in which each stop 63, 65 comprises a single filamentary connection 69 extending transversely in the channel 58. The connection 69 is formed from a single thread. In the configuration shown in FIG. 5(*a*), the ends of the single thread are fixed to the lattice 55 in the region of connection points 71 on the inner surface 57. In the configurations shown in FIGS. 5(*b*) and 5(*c*), the single thread is wound in a loop in order to delimit the filamentary connection 69 placed in the channel 58 and an exterior portion is wound around and to the exterior of the lattice 55 between the connection points 71. In the configuration shown in FIG. 5(*c*), the thread is also fixed by fasteners on the lattice 55, whereas the thread is freely engaged across the lattice 55 in the configuration shown in FIG. 5(*b*).

Figure 6:
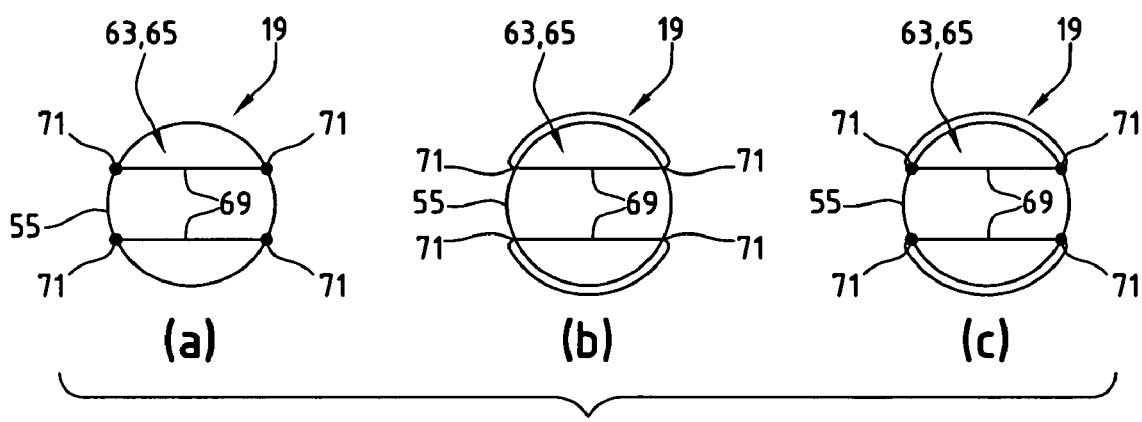

FIG. 6 shows the variants of FIG. 5, in which each stop 63, 65 is formed by two filamentary connections 69 arranged parallel to one another in the channel 58. Each connection 69 is formed by a thread in accordance with the configurations shown in FIG. 5.

Figure 7:
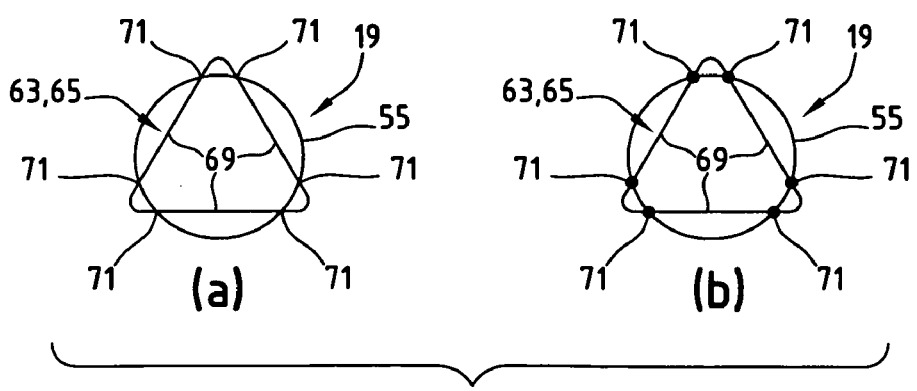

FIG. 7 shows two variants of FIG. 1 in which the construction 67 with three filamentary connections 69 in the form of a triangle is formed from a single thread engaged through the lattice in the region of the vertices of the triangle. The construction 67 thus comprises two connection points 71 in the region of each vertex.

Figure 8:
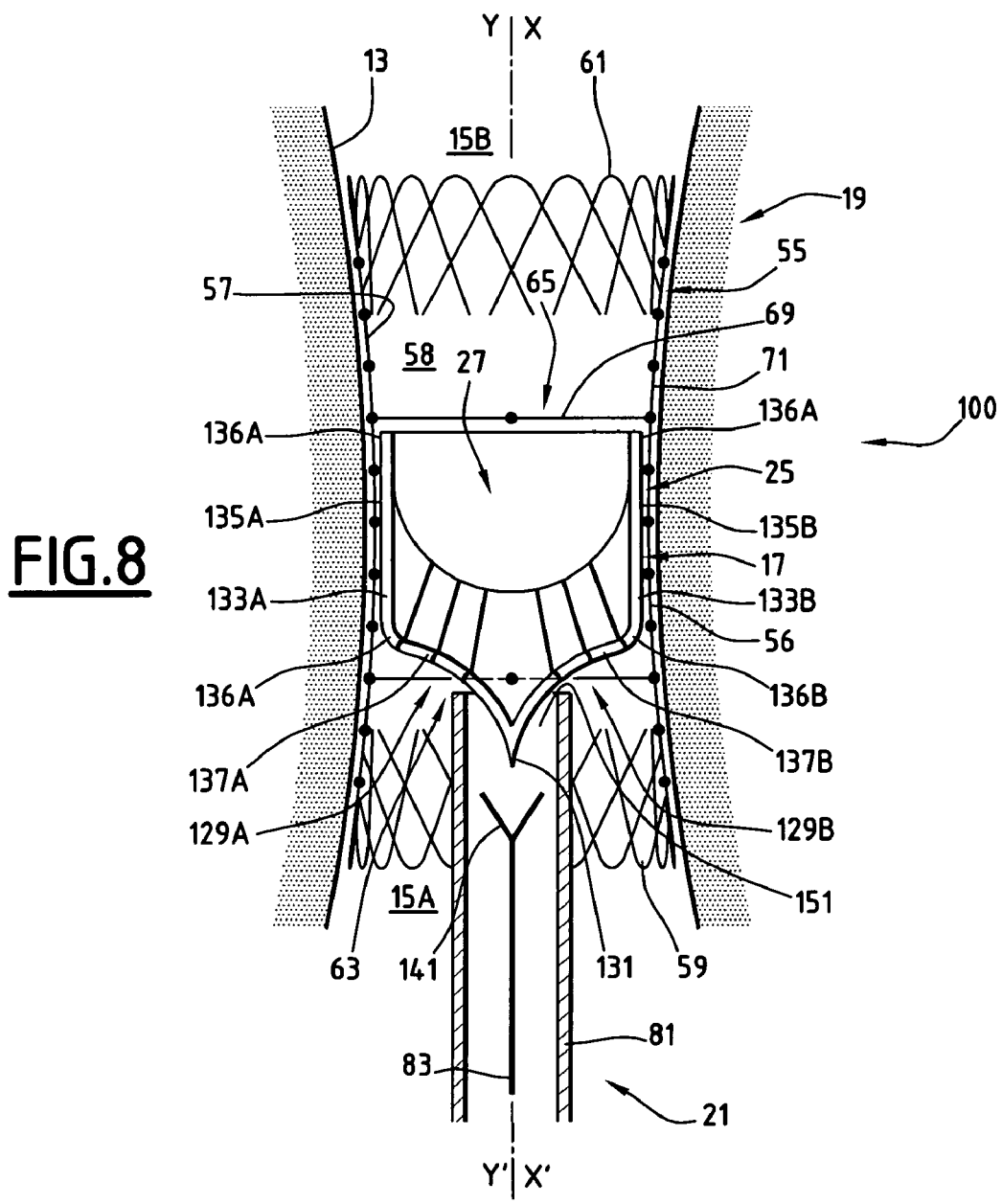
FIG. 8 is a view analogous to that of FIG. 2 of a third kit according to the invention which is provided with a replaceable valve.

In the third kit 100 according to the invention shown in FIG. 8, the valve 17 is a replaceable prosthetic valve. For this purpose, it comprises integrated means for the centripetal compression thereof for retrieving it after it has been implanted.

More specifically, the framework 25 is formed from at least two branches 129A, 129B and, in particular from three branches connected to one another at a first end 131 to form a gripper which can be deformed resiliently between a deployed position in which the branches are at a distance from the median axis X-X', and a folded position in which the two branches 129A, 129B are close to the median axis X-X'. The two branches 129A, 129B are generally symmetrical relative to the median axis X-X', which coincides with the conduit axis after implantation. The branches, measured along the axis X-X', are between 2 and 4 cm in length and preferably 3 cm in length.

Each branch 129A, 129B comprises a support portion 133A, 133B for support against the endoprosthesis 19. Each support portion 133A, 133B is composed of a rectilinear segment extending generally along a generatrix of the endoprosthesis 19 when the framework 25 is deployed. Each support portion 133A, 133B has an outer surface 135A, 135B abutting the endoprosthesis 19. The support portions are from 1 to 3 cm in length and preferably approximately 2 cm in length between a proximal edge 136A and a distal edge 136B. This length is substantially equal to the distance separating the stops 63, 65.

The support portions 133A, 133B are extended by maneuvering portions 137A, 137B which converge towards one another up to the connection point 31. The maneuvering portions are generally inclined relative to the median axis X-X'. The maneuvering portions 137A, 137B are generally curved and have a center of curvature located outside of the space delimited between the two branches. The portions 137A, 137B are therefore rounded towards the interior of the gripper.

In this third kit 100, the tool 21 for fitting the valve 17 is also a tool for retracting the valve. For this purpose, the pulling stent 83 comprises a jaw 141 at the distal end thereof.

The third kit 100 according to the invention is positioned and operates analogously to the first kit 10. However, since the prosthetic valve 17 is equipped with centripetal compression means, it may be reduced to its compressed state and withdrawn translumially.

More specifically, in order to retract the prosthetic valve 17, the catheter 81 is inserted through the right atrium and the right ventricle and is positioned facing the end 131 of the supporting framework in the form of a gripper.

The pulling stent 83 is pushed forward through the catheter 81. The jaw 141 thus grips the end 131 of the gripper. When the open end, denoted with the reference numeral 151, of the catheter 81 is in contact with the maneuvering portions 137A, 137B, the supporting framework is pulled progressively into the catheter 81. Due to the cam effect, the two arms 129A, 129B are drawn towards one another and the prosthetic valve is progressively brought into its compressed state and inserted into the catheter 81. The catheter 81 enclosing the prosthetic valve is then extracted from the human body.

A new catheter containing a new prosthetic valve 17 is then introduced into the human body and the valve is unfurled by carrying out the operations described above in the reverse order.

In a variant, the means for centripetally compressing the valve 17 comprise a tripod as described in the patent application FR-A-2 874 812 or a peripheral cord as described in the patent application FR-A-2 847 800.

The invention claimed is:

1. A kit to be implanted in a blood circulation conduit, said kit comprising:
   a tubular endoprosthesis having an inner surface configured to delimit a channel with a longitudinal axis; and
   a prosthetic valve to be implanted in said tubular endoprosthesis and movable relative to said tubular endoprosthesis, said prosthetic valve including:
      a supporting framework having an outer surface to be applied against said inner surface of said endoprosthesis, said framework being radially deformable from a folded fitting position to a deployed implantation position; and
      a flexible obturator connected to said framework, said obturator being deformable between a closure position in which said obturator extends transversely, and a release position in which said obturator contracts transversely due to a flow circulating through said channel;
   wherein said endoprosthesis includes a stop for locking said prosthetic valve in said channel to prevent axial displacement of said outer surface of said framework along said inner surface of said endoprosthesis in at least a first direction, said stop including a flexible connection extending transversely across said channel between two connection points located on said inner surface of said endoprosthesis and spaced angularly about said longitudinal axis of said channel.

2. The kit of claim 1, wherein said endoprosthesis is deployable between a compressed state and a dilated state, said flexible connection being deployable in conjunction with said endoprosthesis between a slack configuration when said endoprosthesis is in the compressed state and a tight configuration transversely across said channel when said endoprosthesis is in the dilated state.

3. The kit of claim 1, wherein an entire length of said flexible connection located between said two connection points is free relative to said inner surface of said endoprosthesis.

4. The kit of claim 1, wherein said two connection points of said flexible connection are located substantially within a plane perpendicular to said longitudinal axis of said channel.

5. The kit of claim 1, wherein said flexible connection comprises a first flexible connection, said stop further including a second flexible connection, each of said first flexible connection and said second flexible connection extending between two respective connection points, said connection points of said first flexible connection and said second flexible connection being arranged to form vertices of a polygon.

6. The kit of claim 5, wherein said connection points of said first flexible connection and said second flexible connection are all located substantially within a plane perpendicular to said longitudinal axis of said channel.

7. The kit of claim 1, wherein said stop comprises a proximal stop, said endoprosthesis further including a distal stop separated from said proximal stop along said longitudinal axis of said channel, said distal stop including a flexible connection extending transversely across said channel between two connection points located on said inner surface of said endoprosthesis and spaced angularly about said longitudinal axis of said channel.

8. The kit of claim 7, wherein said flexible connection of each of said proximal stop and said distal stop delimits a central passage in said channel, said supporting framework of said prosthetic valve being configured to be inserted between said distal stop and said proximal stop through said central passage when said supporting framework is in the folded fitting position.

9. The kit of claim 7, wherein an axial distance along said longitudinal axis separating said proximal stop and said distal stop is at least as large as an axial length of said outer surface of said supporting framework to be applied against said inner surface of said endoprosthesis.

10. The kit of claim 1, wherein said flexible connection is formed of a thread.

11. The kit of claim 1, wherein said flexible connection comprises a first flexible connection, said stop further including a second flexible connection and a third flexible connection, each of said first flexible connection, said second flexible connection, and said third flexible connection extending between two respective connection points, said connection points of said first flexible connection, said second flexible connection, and said third flexible connection being arranged to form vertices of a triangle located substantially within a plane perpendicular to said longitudinal axis of said channel.

12. The kit of claim 1, wherein said flexible connection comprises a first flexible connection, said stop further including a second flexible connection, a third flexible connection, and a fourth flexible connection, each of said first flexible connection, said second flexible connection, said third flexible connection, and said fourth flexible connection extending between two respective connection points, said connection points of said first flexible connection, said second flexible connection, said third flexible connection, and said fourth flexible connection being arranged to form vertices of a foursided polygon located substantially within a plane perpendicular to said longitudinal axis of said channel.

13. The kit of claim 1, wherein said flexible connection comprises a first flexible connection, said stop further including a second flexible connection, each of said first flexible connection and said second flexible connection extending between two respective connection points so that said first flexible connection and said second flexible connection are parallel.

* * * * *